United States Patent [19]
Rix et al.

[11] Patent Number: 5,979,240
[45] Date of Patent: Nov. 9, 1999

[54] METHOD AND APPARATUS FOR DETECTING RECYCLABLE ITEMS CONCEALED WITHIN SOLID WASTE

[75] Inventors: Scott M. Rix, Arlington, Va.; Earl N. Powers, White Hall, Md.

[73] Assignee: System Planning Corporation, Arlington, Va.

[21] Appl. No.: 08/855,523

[22] Filed: May 13, 1997

Related U.S. Application Data

[63] Continuation of application No. 08/566,151, Dec. 1, 1995, abandoned.

[51] Int. Cl.$^6$ .................................................. G01N 29/00
[52] U.S. Cl. ................................ 73/602; 73/579; 209/930
[58] Field of Search ........................... 73/659, 648, 602, 73/630, 628, 645, 579, 596, DIG. 1; 209/590, 930; 367/87

[56] References Cited

U.S. PATENT DOCUMENTS

| | | | |
|---|---|---|---|
| 2,861,256 | 11/1958 | Hart | 367/135 |
| 2,994,060 | 7/1961 | Ross | 367/101 |
| 3,268,856 | 8/1966 | Wallen, Jr. | 367/135 |
| 3,425,507 | 2/1969 | Caldwell et al. | 367/7 |
| 3,712,469 | 1/1973 | Dwyer et al. | 209/590 |
| 4,041,774 | 8/1977 | Morris et al. | 73/610 |
| 4,368,641 | 1/1983 | McLeod, Jr. | 73/597 |
| 4,557,386 | 12/1985 | Buckley et al. | 209/556 |
| 4,576,286 | 3/1986 | Buckley et al. | 209/558 |
| 4,584,676 | 4/1986 | Newman | 367/108 |
| 4,651,568 | 3/1987 | Reich et al. | 73/612 |
| 4,690,284 | 9/1987 | Buckley et al. | 209/590 |
| 4,730,190 | 3/1988 | Win et al. | 342/118 |
| 4,819,649 | 4/1989 | Rogers et al. | 128/660.02 |
| 5,068,835 | 11/1991 | Reed | 367/135 |
| 5,125,514 | 6/1992 | Oehler et al. | 209/590 |
| 5,152,401 | 10/1992 | Affeldt, Jr. et al. | 209/556 |
| 5,195,059 | 3/1993 | Hiroshi et al. | 367/99 |
| 5,355,987 | 10/1994 | DeWoolson et al. | 194/209 |
| 5,465,822 | 11/1995 | DeWoolson et al. | 194/209 |
| 5,501,344 | 3/1996 | Kaiser et al. | 209/578 |
| 5,615,778 | 4/1997 | Kaiser et al. | 209/578 |
| 5,632,381 | 5/1997 | Thust et al. | 209/44.1 |

FOREIGN PATENT DOCUMENTS

| | | | |
|---|---|---|---|
| 212 516 | 2/1987 | European Pat. Off. | 209/590 |
| 484 611 | 5/1992 | European Pat. Off. | 209/590 |
| 29 02 901 | 7/1980 | Germany | 209/590 |
| 41 25 045 | 2/1993 | Germany | 209/930 |

OTHER PUBLICATIONS

Basic Concepts of Acoustic Resonance Spectroscopy (ARS) For Chemical Weapons Munition Analysis, Apt et al., Los Alamos National Laboratory, preprint of paper intended for printing in a journal of proceedings (No Date avail).

Acoustic Resonance Spectroscopy (ARS), Sinha, Apr. 1992 IEEE Potentials, pp. 10–13.

*Primary Examiner*—Hezron Williams
*Assistant Examiner*—Richard A. Moller
*Attorney, Agent, or Firm*—Pollock, Vande Sande & Amernick

[57] ABSTRACT

A device for detecting the presence of items made of recyclable materials randomly located and arranged within randomly arranged solid waste having random characteristics. A transmitter produces acoustic energy of at least one predetermined wavelength in a desired direction. The acoustic energy causes the items made of recyclable material present within the randomly arranged solid waste to resonate and thereby produce resonated acoustic energy. A receiver receives the resonated acoustic energy. The receiver generates a signal based upon the resonated acoustic energy. A processor connected at least to the receiver receives the signal from the receiver for analyzing the resonated acoustic energy, for calculating the signal based upon the resonated acoustic energy, and comparing the calculated signature to known signatures of items made of recyclable materials. An indicator indicates when the calculated signature substantially corresponds to at least a selected one of the known signatures, thereby indicating the presence of items made of recyclable materials.

18 Claims, 12 Drawing Sheets

METHOD AND APPARATUS FOR DETECTING RECYCLABLE ITEMS CONCEALED WITHIN SOLID WASTE

This application is a continuation of U.S. patent application Ser. No. 08/566,151, filed Dec. 1, 1995 now abandoned.

FIELD OF THE INVENTION

The present invention relates to a method and apparatus for detecting the presence of items made of recyclable materials within solid waste. In particular, the invention relates to detecting the presence of items made of recyclable materials within residential and industrial trash.

BACKGROUND OF THE INVENTION

As local solid-waste landfill space reaches capacity, many communities have enacted mandatory recycling programs. Such programs typically require all users of the municipal solid-waste disposal services to pre-sort their trash and remove specified recyclable materials. Recycling programs have many advantages. Among the advantages are source reduction in the volume of solid waste placed in landfills, reduced energy consumption generating raw materials, and reduced environmental degradation from reuse of raw materials.

However, often, people fail to comply with recycling programs. As a result, many communities are searching for methods to encourage or enforce recycling practices. To realize these benefits, communities have passed laws that require users to pre-sort recyclable materials from solid-waste. Such laws help to promote recycling at the source and eliminate the need to separate recyclable items from the solid waste after it has been collected and sort the recyclable items. Such separating and sorting activities can be expensive, unpleasant, time consuming, and inefficient.

Additionally, collecting recyclable waste costs money. Municipalities and other parties may recover at least some of this money by selling the recyclable materials that they collect. Also, as recycling increases, the price for many recyclable materials is dropping. Therefore, municipalities and other interested parties may wish to maximize the return they obtain from their recycling programs.

Requiring source pre-sorting of recyclable materials provides many advantages. However, one drawback of such requirements is the inability to enforce them effectively. For example, although many communities have passed legislation that requires users to pre-sort their waste, this legislation relies on voluntary compliance. In an effort to enforce mandatory sorting and recycling laws, some communities use government officials to inspect, or "sample", trash bags suspected of containing recyclable materials. However, this task is unpleasant, slow, and inefficient. Currently, there is no effective, safe, and efficient means to quickly inspect waste bags to determine if they contain recyclable materials.

SUMMARY OF THE INVENTION

The present invention was developed at least in part in an effort to overcome the above-described problems. Accordingly, one object of the present invention is to provide an acoustic measurement technique that may be used to identify the presence of recyclable items concealed in solid waste and solid waste receptacles.

Another object of the invention is to provide a safer, less expensive, more reliable, and more sanitary device to support or supplant the manual inspection of recyclable items concealed within non-recyclable waste.

A further object of the invention is to provide an easy-to-use, battery operated system to inspect municipal waste for recyclable items.

An additional object of the invention is to provide municipal governments with an efficient means to monitor and enforce mandatory recycling laws.

A still further object of the invention is to provide a means to scan solid-waste disposal operations to detect recyclable items that are accidentally or purposely being discarded with non-recyclable solid waste.

In accordance with these and other objects and advantages, preferred aspects of the present invention provide a device for detecting the presence of items made of recyclable materials within solid waste. The device includes a transmitter for producing acoustic energy of at least one predetermined wavelength and transmitting the acoustic energy in at least one desired direction. A receiver receives an acoustic response generated by the acoustic energy, produced by the transmitter, interacting with materials included in the solid waste. The receiver generates a signal based upon the acoustic response. A processor is connected at least to the receiver for receiving the signal from the receiver. The processor also analyzes the acoustic response and calculates a signature based upon the acoustic response. Additionally, the processor compares the calculated signature to known signatures calculated by analyzing acoustic responses generated by acoustic energy interacting with known materials. The device further includes means for indicating when the calculated signature substantially corresponds to at least a selected one of the known signatures.

According to other preferred aspects, the present invention provides a device for detecting the presence of items made of recyclable materials in waste. The device includes means to excite a target suspected of containing at least one recyclable item with acoustic energy, thereby producing an acoustic response from the target. Additionally, the device includes means to measure the acoustic response. Furthermore, the device includes means to compare the acoustic response of the target with known acoustic responses of recyclable materials. The device also includes means to indicate a substantial correspondence between an acoustic response from the target with at least one of the known acoustic responses.

According to further preferred aspects, the present invention provides a method for detecting items made of recyclable materials in solid waste. The method includes generating acoustic energy of at least one predetermined wavelength. The acoustic energy is directed in the direction of the solid waste, to generate an acoustic response in materials within the solid waste. The acoustic response is received by a receiver. A signature of the acoustic response is calculated by analyzing the acoustic response. The calculated signature is compared with known signatures calculated by analyzing acoustic responses generated by acoustic energy interacting with known materials.

Still other objects and advantages of the present invention will become readily apparent to those skilled in this art from the following detailed description, wherein it is shown and described only the preferred embodiments of the invention, simply by way of illustration of the best mode contemplated of carrying out the invention. As will be realized, the invention is capable of other and different embodiments, and it's several details are capable of modifications in various obvious respects, without departing from the invention.

Accordingly, the drawings and description are to be regarded as illustrative in nature and not as restrictive.

DETAILED DESCRIPTION OF THE INVENTION

Figure 1A:
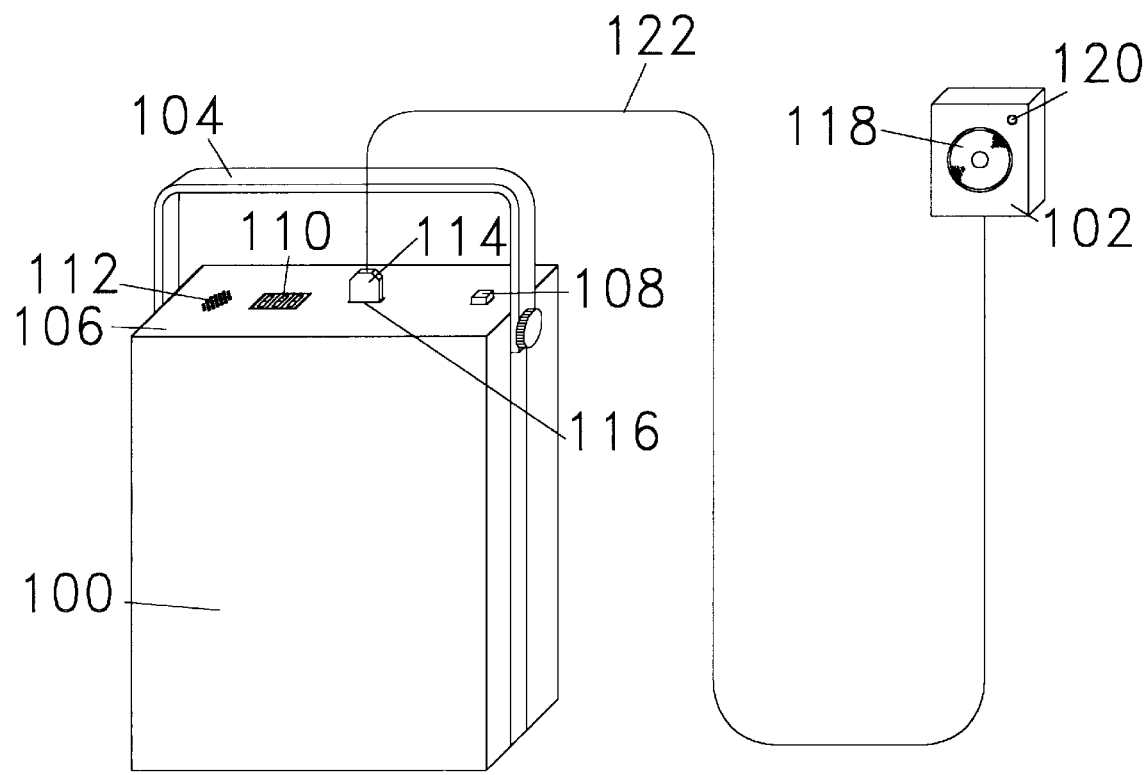
FIG. 1A represents a perspective view of one embodiment of a portable self-contained recyclable item detector according to the present invention.

The present invention relates to a method and apparatus for detecting the presence of items made of recyclable materials among other, non-recyclable solid waste. The items may include, for example, bottles, cans, containers, and articles. The materials may include, among others, glass, plastic, aluminum, steel, paper and other materials used to produced typical containers. Such materials are especially valuable to recycling programs because these materials can be reprocessed easily.

The present invention provides a device that permits solid waste, such as municipal and/or industrial trash, to be inspected and the presence of items made of recyclable materials to be detected using an acoustic measurement technique. The device preferably emits a pulse of acoustic energy and measures an acoustic response produced by the acoustic pulse interacting with the items within the waste. As described in detail below, the measured acoustic response may be analyzed to identify items made of recyclable materials, thereby revealing their presence. As such, the present invention may be useful for monitoring and enforcing mandatory recycling laws as well as inspecting solid-waste stream disposal processes.

In the process of detecting items made of recyclable materials, the present invention may detect one or both of at least two difference acoustic responses from the items. These two acoustic responses include resonance and reflectance. Other acoustic responses may also be detected.

According to the acoustic response of reflectance, an acoustic interrogation pulse of one or more frequencies may be directed toward the solid waste. The acoustic pulse may be a pulse or a sweep, as described below. The acoustic pulse then reflects off of one or more surfaces on the items of recyclable materials. Next, reflected acoustic pulse is detected, analyzed, and compared to acoustic pulses reflected off of known materials. If the detected pulse is in the vicinity of one or more of the known pulses, then likelihood that items made of recyclable materials are in the solid waste may be increased. How closely the reflected pulses must match known pulses is discussed in greater detail below.

According to the acoustic response that includes resonance, an acoustic interrogation pulse is directed at the solid waste. The acoustic pulse interacts with items made of recyclable materials, causing them to resonate. The sound waves produced as the materials resonate are detected, analyzed, and compared to known acoustic resonances of known recyclable materials. If the detected resonance substantially matches the resonance of known materials, then the likelihood that the solid waste includes items of recyclable materials may be increased. How closely the detected resonance must match the known resonances is discussed in greater detail below.

Devices and methods according to the present invention that employ resonance are based upon the fact that mechanical systems may oscillate in response to a periodically varying force. Generally, the amplitude of a forced oscillation in a particular mechanical system is small. However, if the frequency of the periodic force is at or near a natural oscillation frequency of the mechanical system, a large amplitude response is generated. The tendency for a mechanical system to produce a large amplitude response from a forced oscillation near a natural frequency mode is called resonance.

Elastic structures typically have resonance modes and can oscillate with certain natural frequencies. These resonance modes can be excited with a mechanical driving force at or near the natural frequency of the structure. The present invention may use acoustic vibrations in air to excite items made of recyclable materials. The present invention is particularly useful for detecting concealed items made of recyclable materials within non-recyclable solid waste.

To induce resonance mode oscillations in an elastic structure, the structure typically is excited at appropriate frequency(ies). The frequency(ies) may be audible. Any general means of acoustic excitement preferably includes the appropriate frequency(ies) or frequency components at the frequency of the item that is being detected or trying to be detected. The acoustic excitement preferably is directed to the solid waste to in effect interrogate the waste.

Two common techniques of acoustic excitement that may be useful for this invention are the acoustic impulse and the swept frequency. According to the acoustic impulse technique or "ping", an acoustic impulse can be used to generate or excite a broadband frequency spectrum in the range of interest. The present invention may rely on the acoustic impulse technique to isolate the resonances of an item made of a particular recyclable material. The excitation impulse preferably spreads the acoustic energy across a wide range of frequencies. The recyclable item may act as a narrow selective filter that strongly reradiates only at is characteristic frequency or frequencies.

This resonance frequency may be detected and used as a signature that indicates a recyclable item is present within the solid waste by comparing the characteristic frequency or frequencies with the characteristic frequency or frequencies generated by items of known materials. Preferably, the characteristic frequency or frequencies generated by items of known materials are determined prior to the interrogation of the waste and the frequency or frequencies generated by the interrogation pulse are then compared to the characteristic frequency or frequencies generated by items of known materials. An impulsive acoustic means allows the easy separation of the driving pulse and subsequent response from the "ringing" expressed by the item made of a recyclable material.

The other technique that the present invention may use to detect the presence of items made of recyclable materials is generation of an acoustic chirp that sweeps through a range of frequencies. According to the swept frequency technique a range of frequencies is "swept" through, or produced. By sweeping the acoustic signal through a broad range of frequencies, it is possible to match or "tune" the resonance frequency of an item made of a particular recyclable material. When the resonance frequency is produced, it preferably causes the item made of that material to reradiate at that frequency. The item may reradiate strongly.

FIG. 1A shows a perspective view of an embodiment of a device according to the present invention. The embodiment shown in FIG. 1A is portable. Other embodiments may be more or less portable. The device shown in FIG. 1A is contained within a primary housing 100 and a satellite housing 102. However, the device may be housed within a single housing or may include more than two housings for enclosing one or more of the components of the device.

A handle 104 may be connected to primary housing 100 to facilitate carrying the device, or at least the components primary housed within the primary housing of the embodiment shown in FIG. 1. A top plate 106 may contain controls and displays. For example, the controls and displays may include controls for the device and displays to indicate operating parameters, functioning and results of the device. However, the controls and displays may be located elsewhere on the device, or in or on a separate housing.

Among the controls are a power switch 108 that may be located on top plate 106 to allow the user to turn the device on or off. The displays may include a digital display 110 that indicates to the user the calculated detection probability for the most recent acoustic scan.

The device preferably also includes means for indicating whether the device has detected, or there is a high probability that the device has detected, the presence of an item made of a recyclable material within solid waste. The indicating means may include an audible indicator and/or a visual indicator. Although, the device may include other indicating means.

An example of an indicating means is an alarm. The embodiment shown in FIG. 1A includes an audible alarm that includes a speaker 112. The audible alarm preferably audibly warns the user of the device that a detection probability threshold has be attained, indicating a that a recyclable item may be present.

Primary housing 100 of the embodiment shown in FIG. 1A may also include a socket 116 and a connector 114 that may be used to attach the components housed within primary housing 100 to satellite housing 102 through a satellite cable 122. Socket 116 and connector 114 may permit a user of the device to disconnect the satellite housing from the primary housing for storage when the device is not in use. When the device is being used, socket 116, connector 114, and satellite cable 122 may provide an electrical connection to satellite housing 102. Of course, if the device is housed within one housing, then satellite cable 122, connector 114, and socket 116 are not necessary.

A device according to the invention includes means for exciting a target with acoustic energy. The exciting means may include means for producing an acoustic impulse. For example, the exciting means may include a transmitter. The transmitter preferably produces an acoustic impulse. The acoustic impulse may include sound waves of one or more wavelength and/or one or more frequency. Additionally, the acoustic impulse may include more than one frequency or wavelength generated substantially simultaneously or at intervals.

The acoustic impulse may consist of vibrations generated by an acoustic transducer. The acoustic transducer may include a loudspeaker or piezoelectric device. However, any device capable of producing a desired acoustic impulse may be used.

The acoustic energy may be coupled, or transmitted, to the recyclable items via an air propagation path. As described above, the acoustic energy may induce oscillations within items formed from recyclable materials (s). The recyclable items may reradiate at least some of the acoustic energy at their respective resonance frequency(ies).

In the embodiment shown in FIG. 1A, the acoustic transducer is housed within satellite housing 102. However, if the device includes only one housing, the acoustic transducer may be housed within the one housing. Alternatively, the device may include more than one housing.

In the embodiment shown in FIG. 1A, the acoustic transducer is a transmitter or transmit speaker 118. The transmitter or transmit speaker 118 is housed within satellite housing 102, shown in FIG. 1A and FIG. 1B. Transmitter or transmit speaker 118 preferably converts an electrical signal received from primary housing 100 through satellite cable 122 into an acoustic impulse. Preferably, the acoustic impulse radiates from the transmitter or transmit speaker 118 at the front of the satellite housing as shown in FIG. 1A. Transmitter or transmit speaker 118 may be a typical, audio-quality component found in any electronics store, such as Radio Shack.

As stated above, the acoustic impulse interacts with the materials in the solid waste. As a result, an acoustic response is generated. Therefore, to detect the acoustic response, the present invention preferably includes means to measure the acoustic response. The means to measure the acoustic response may be housed within the satellite housing 102. However, if the device includes only one housing, the means for measuring the acoustic response may be housed within the one housing. Alternatively, the device may include more than one housing.

The present invention may use an acoustic transducer, such as a sensitive microphone, as the means for detecting the acoustic response and to detect any familiar resonance mode oscillations from within non-recyclable solid waste. In the embodiment shown in FIG. 1A, the means for measuring the acoustic response includes a receiver or microphone 120. The receiver or microphone may be housed within satellite housing 102. Receiver or microphone 120 preferably converts the acoustic response into an electrical signal. If the measuring means is housed in satellite housing 102, then the electrical signal preferably is transmitted from satellite housing 102 through satellite cable 122 to the primary housing 100. If the measuring means includes a microphone or receiver, such components may be a typical, audio-quality component found in any electronics store, such as Radio Shack.

Figure 1B:
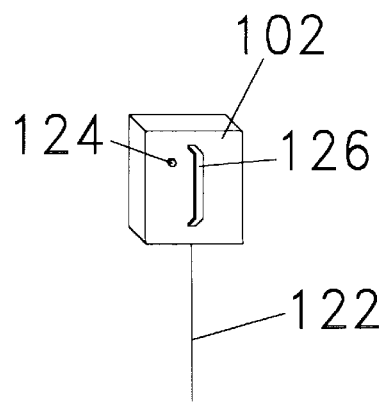
FIG. 1B represents a perspective view of the rear side of the satellite housing of the embodiment shown in FIG. 1A.

The device preferably includes means for activating the device. The activating means in the embodiment shown in FIG. 1B is a trigger 124. Trigger 124 may be used by the user to send an electrical signal to housing 100 through satellite cable 122 to indicate measurement is required. Trigger 124 may be a simple push-button electrical switch.

Although the activating means in the embodiment shown in FIG. 1B is a trigger provided on the satellite housing, the activating means may be provided on primary housing 100. The activating means may not even be provided on any housing and could be attached to a separate device or other structure. Also, the activating means could be a device other than a trigger. For example, the device could include a sensor that automatically triggers the device.

To allow the user to grasp satellite housing 102 comfortably, a satellite housing handle 126 may be provided on the back of satellite housing 102, as shown in FIG. 1B. Similarly, primary housing 100 may also include a handle 104. However, if the device is housed in other housing, then the housing may not include a handle. For example, the components housed in primary housing 100 may be housed on a garbage truck. In this case, the garbage truck would not include a handle.

The present invention may also include a power source. The power source may be a battery 127 in the embodiment shown in FIG. 3. For example, a lead-acid rechargeable battery may be used. Alternatively, a disposable battery may be used. If included on a garbage truck or other vehicle, the present invention may be powered by the vehicle. However, battery power is preferable if the device is to be hand held.

Figure 3:
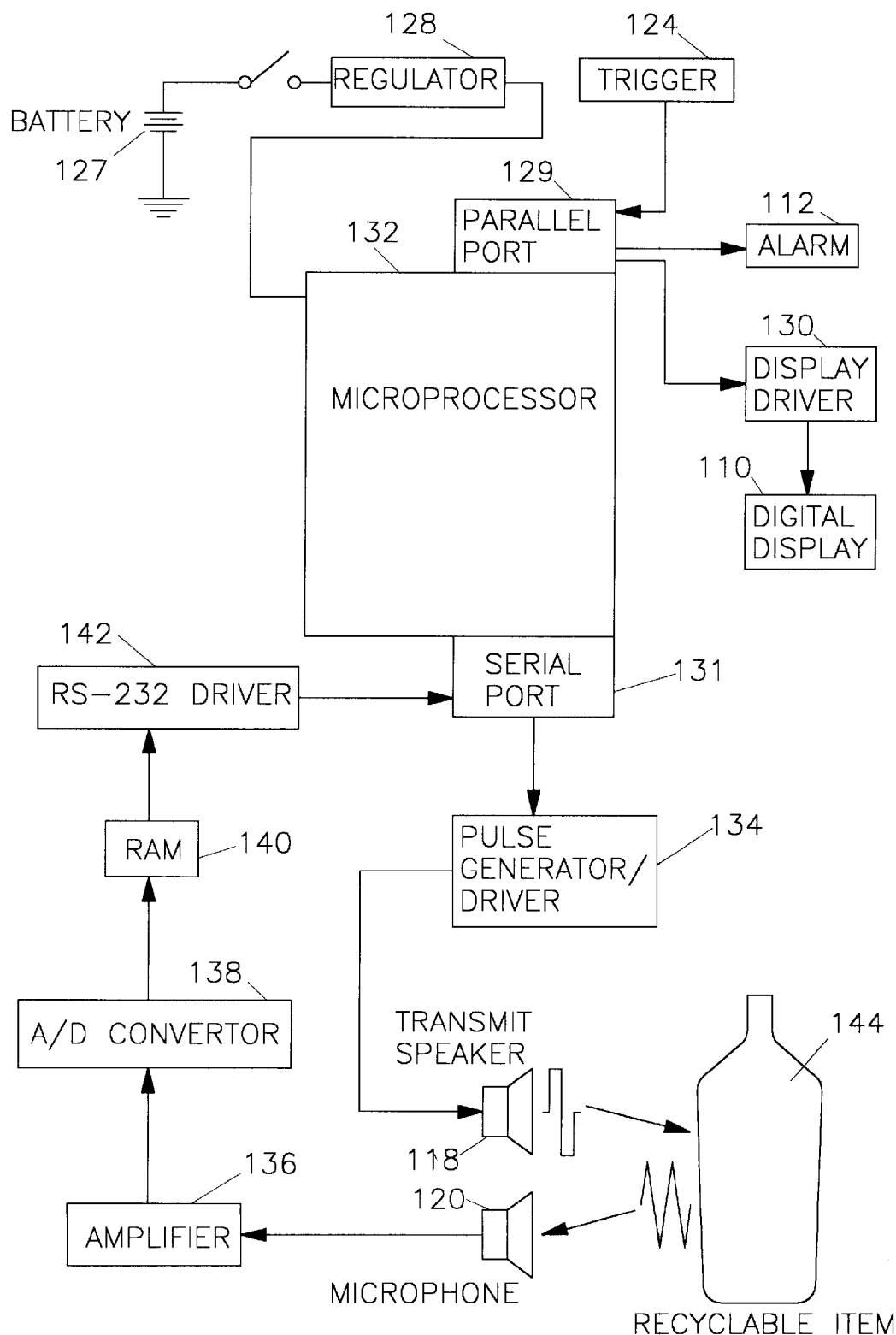
FIG. 3 represents a block diagram showing major components of an embodiment of a recyclable item detector according to the invention.

The voltage produced by the power source may be altered to an appropriate level by a regulator 128 in the embodiment shown in FIG. 3. In particular, the regulator may alter the voltage to appropriate levels depending upon the electronic circuitry making up the device. From the regulator, the electric current may be distributed to appropriate locations in the device.

The device may be controlled with a controller. The controller may be a microcomputer or microprocessor. The controller may perform other functions in addition to control, such as processing an acoustic response received from solid waste. In the embodiment shown in FIG. 3, the controller is a microprocessor 132. One example of a microprocessor is an IBM PC 8088 clone incorporated on a single board. However, any microprocessor may be used as the controller of the present invention. Microprocessor 132 may include a fully functional bus (not shown), serial port 131, parallel port 129, RAM (not shown), and programmable ROM (not shown). Microprocessor 132 may be connected to trigger 124 through parallel port 129.

Figure 5:
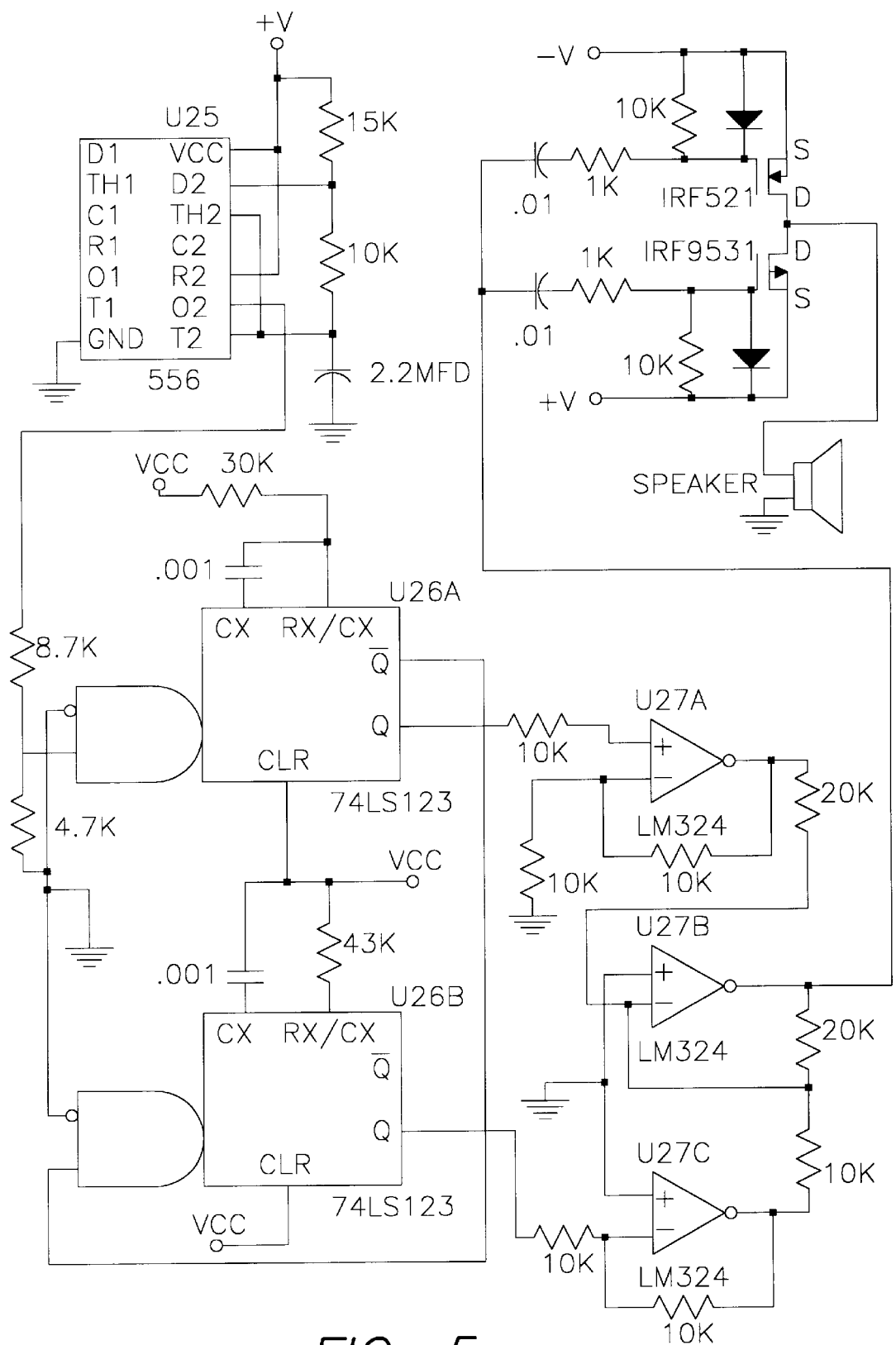
FIG. 5 represents a schematic of a speaker driver circuit that generates a doublet acoustic pulse of about 0.3 ms.

Serial port 131 may be used to connect microprocessor 132 to a pulse generator and speaker driver circuit 134. An embodiment of an electrical schematic of pulse generator and speaker driver circuit 134 is shown in FIG. 5. Pulse generator and speaker driver circuit 134 may be connected to the means for exciting the target. In the embodiment shown in FIG. 5, the excitation means is a transmit speaker 118 that radiates an acoustic impulse signal.

In the embodiment shown in FIG. 3, the means to measure an acoustic response is a microphone 120. In this embodiment, the microphone measures a return acoustic signal, or acoustic response, and converts the energy in the acoustic response into an electrical signal. The electrical signal may be sent to an amplifier circuit 136 to increase its amplitude. Amplifier circuit 136 may be a standard, low-noise, circuit design available, for example, from Burr-Brown, Inc.

To permit the signal to be processed by a microprocessor, the present invention may include an A/D converter 138. The amplified signal may be digitized with A/D converter 138. The signal may then be sent to the microprocessor to be processed.

Figure 6A:
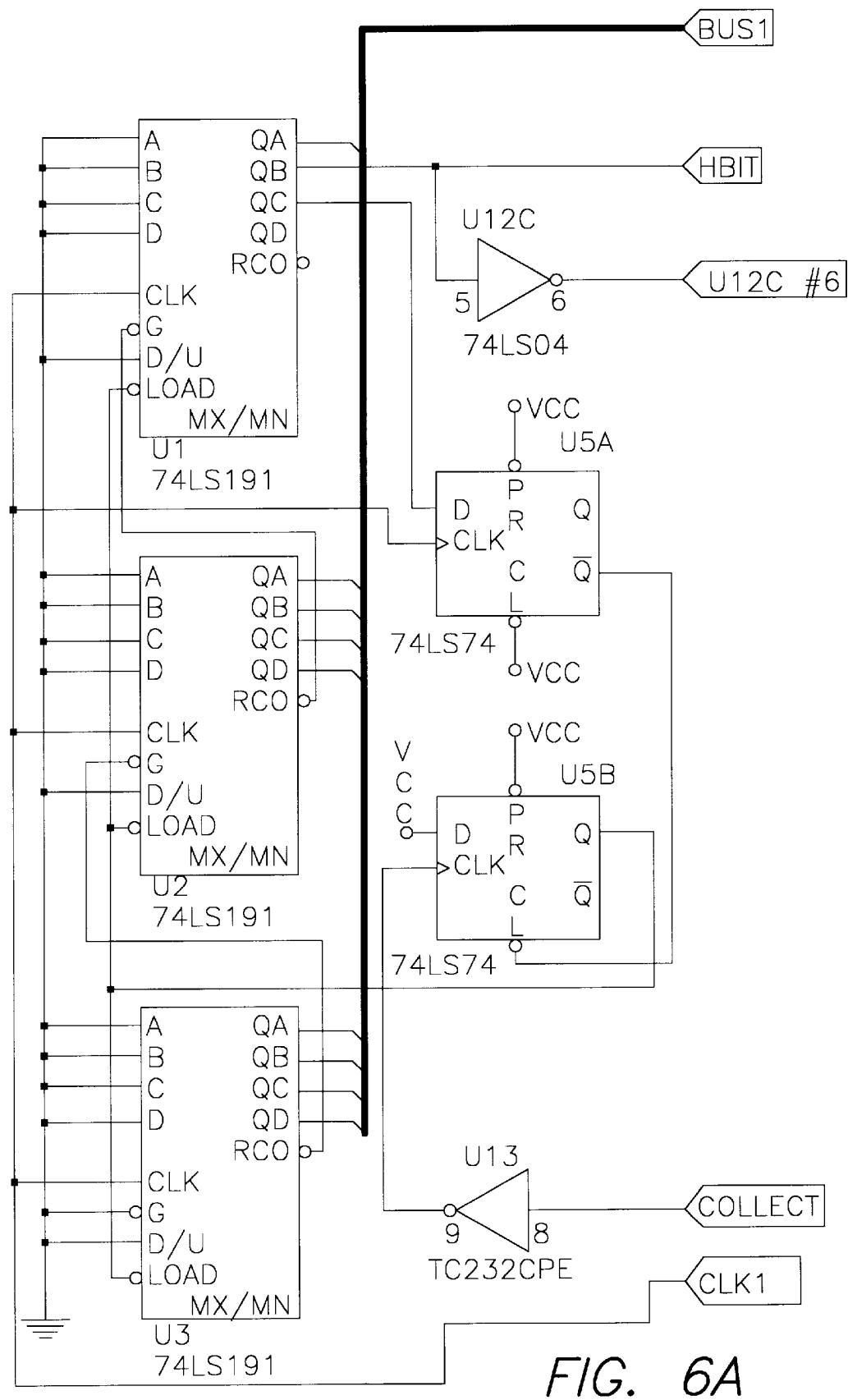
FIG. 6 represents a schematic of an A/D conversion and storage circuit that digitizes and stores a signal measured by a microphone.
Figure 6B:
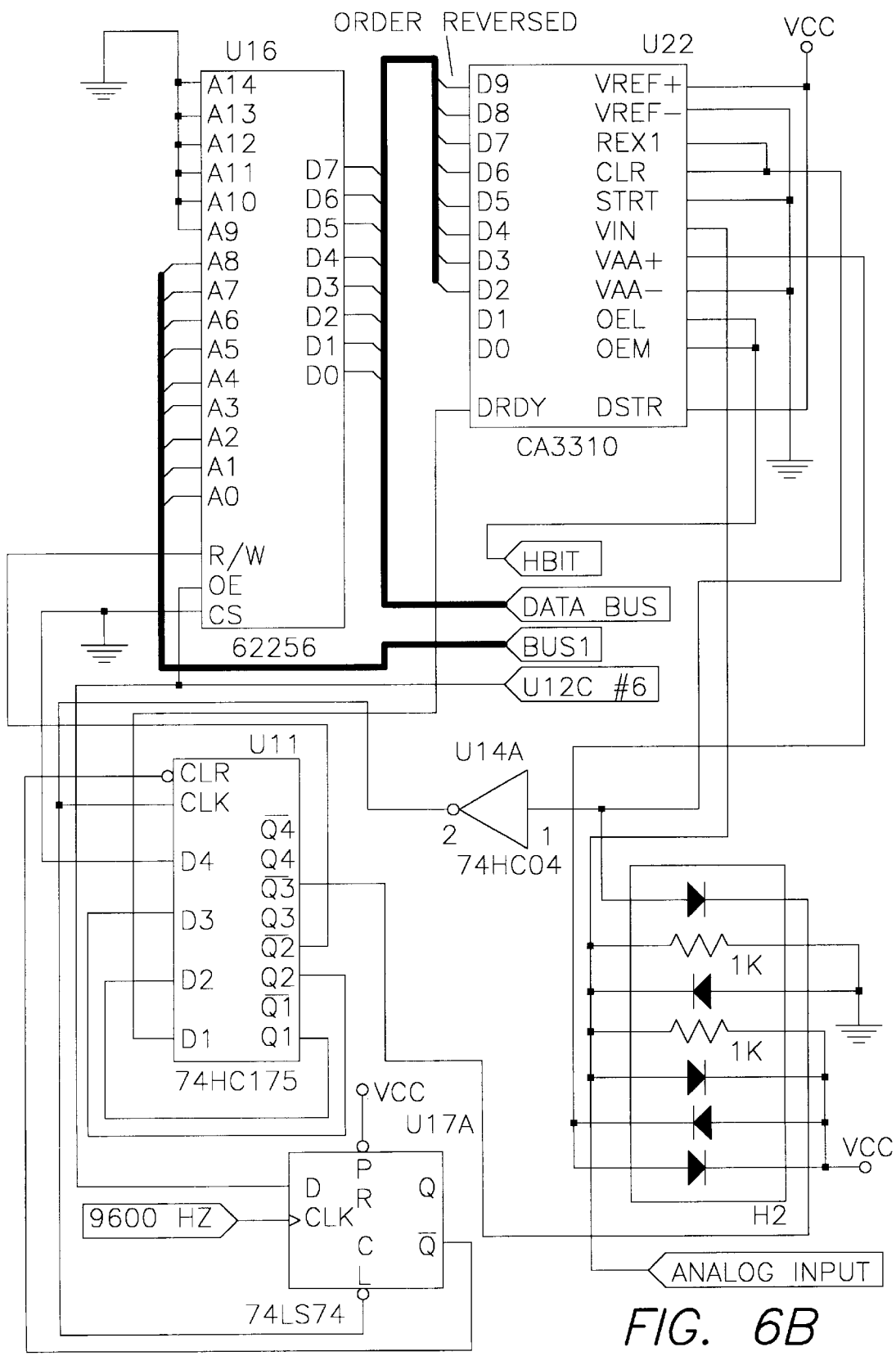
Figure 6C:
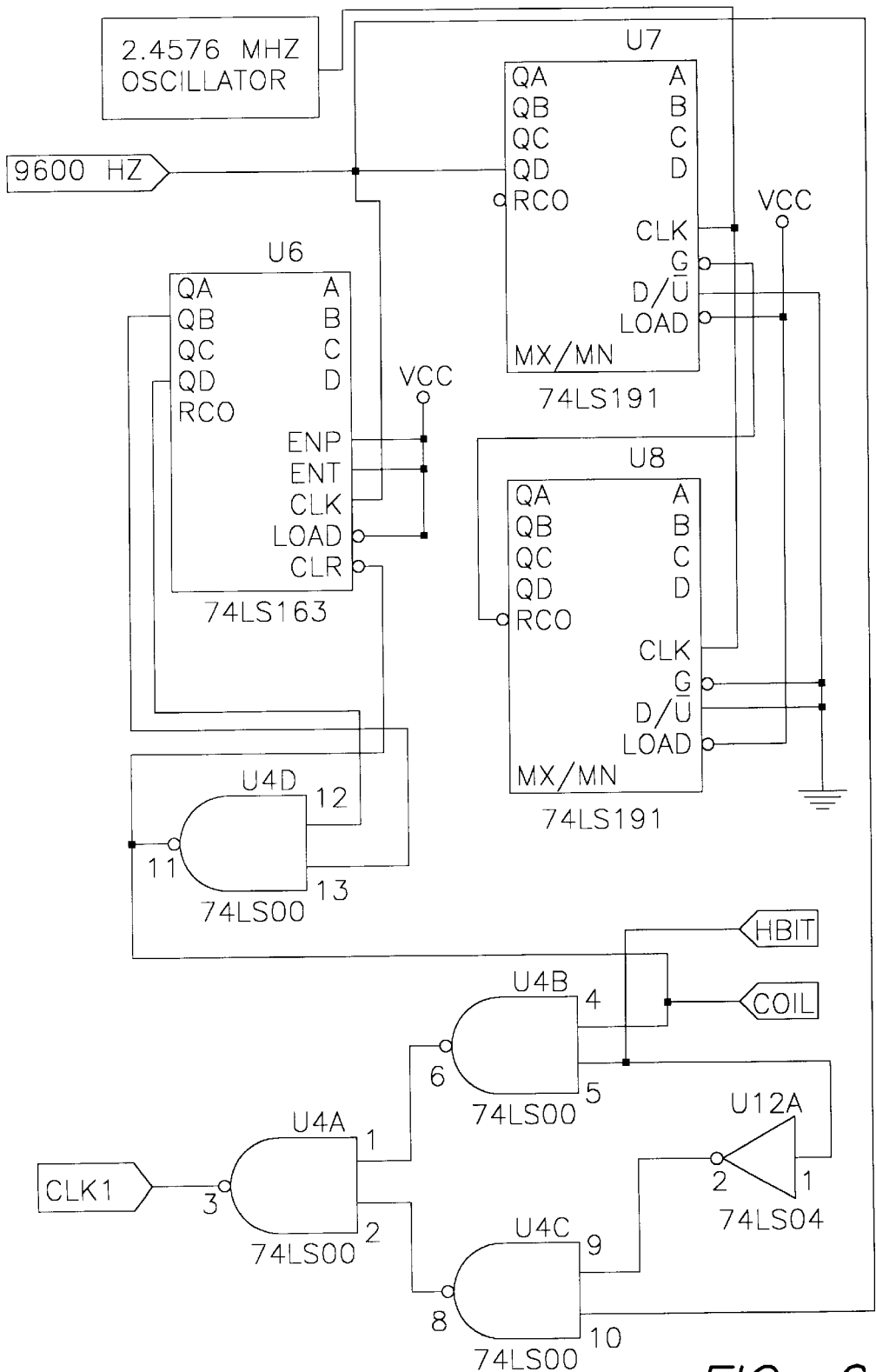

Alternatively, the digitized signal may be stored in a temporary random access memory (RAM) 140 to await transfer to microprocessor 132. An embodiment of an electrical connection schematic for A/D converter 138 and RAM 140 is shown in FIG. 6. The signal preferably is stored sequentially in the RAM until a desired sample size has been recorded. For a given sampling frequency, the sample length may affect the frequency resolution of the measurement, with a longer sampling lengths typically produce a higher frequency resolution. For example, the present invention may sample at about 10,000 samples per second for about 25.6 milliseconds. This sampling protocol may produce a total of about 256 8-bit sample points sequentially stored in RAM. Also, this sampling protocol may produce a theoretical frequency resolution of about 128 segments over about a 5 kHz spectrum, or about 39 Hz.

Figure 7:
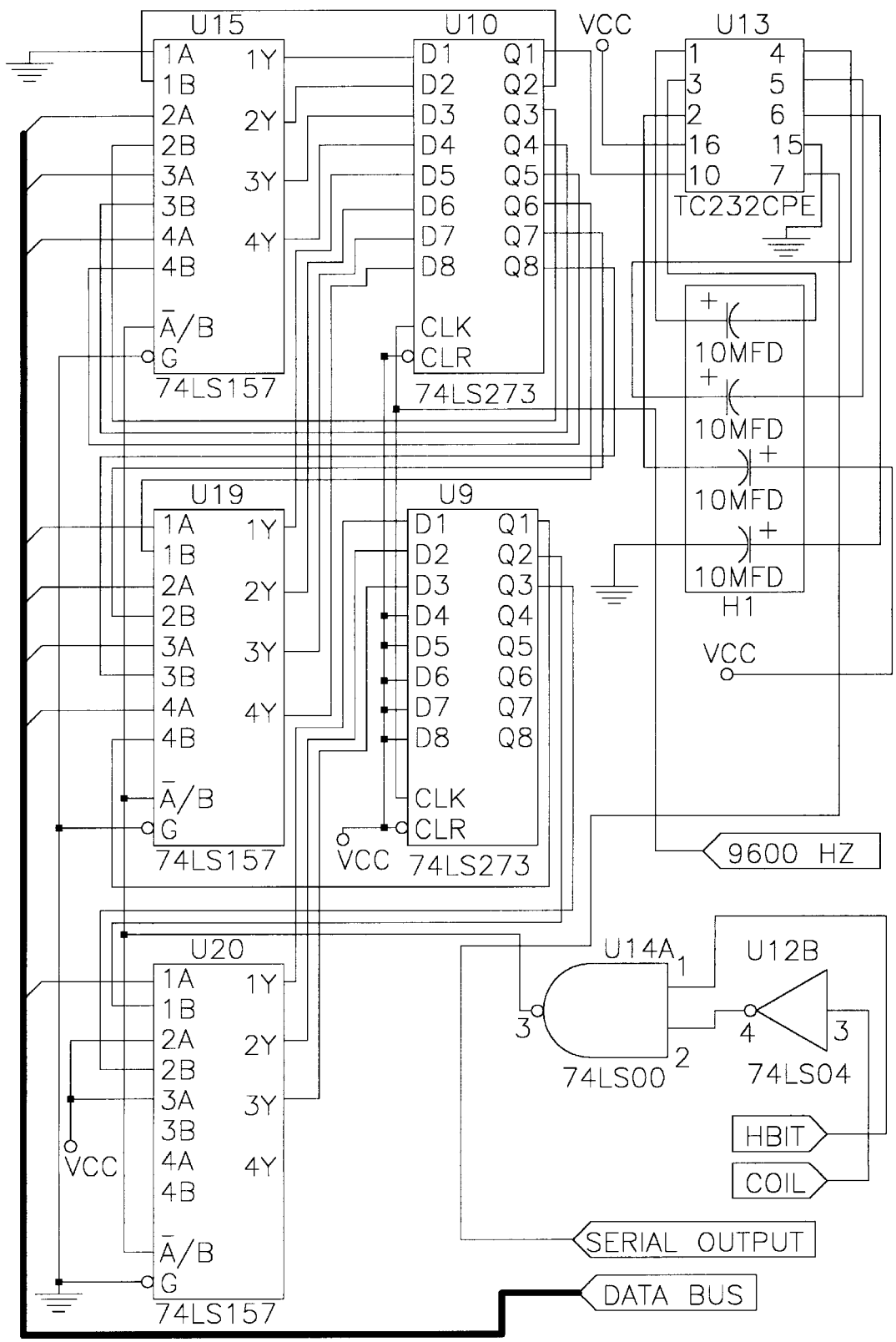
FIG. 7 represents a schematic of a RS-232 transmission circuit that may transfer A/D data to a serial port of a microcomputer.

Upon attaining the desired sample length, the digitized signal in RAM 140 may be transferred to microprocessor 132. The connection between the RAM and the microprocessor may be an RS-232 driver circuit 142. An embodiment of an electrical schematic for RS-232 driver circuit 142 is shown in FIG. 7.

As stated above, the invention preferably includes means for indicating the presence of a recyclable material. The indicating means may include one or more audible, visual, or other indicators. In the embodiment shown in FIG. 3, the alarm is audible alarm 112. Regardless of the type of indicating means included in the device, the indicating means may indicate when the device detects the presence of recyclable materials and/or when the recyclable materials are not detected. The indicating means may be connected to microprocessor 132 to receive a signal from the microprocessor indicating the results of the processing of the acoustic response and the comparison to known acoustic responses of known recyclable materials. In the embodiment shown in FIG. 3, the indicating means and the microprocessor are connected through parallel port 129.

Figure 8:
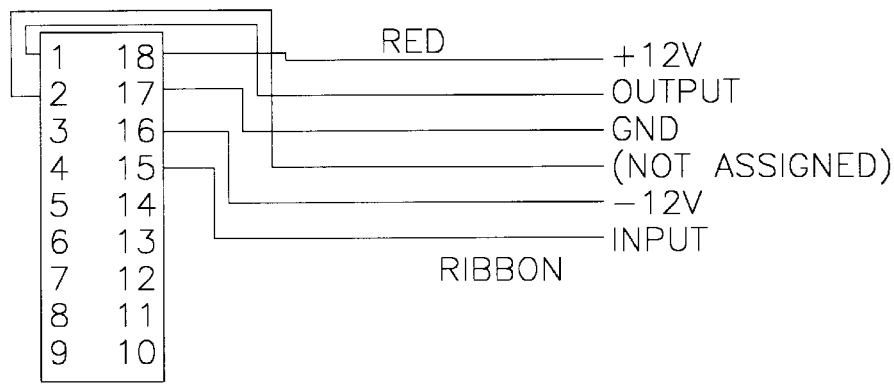
FIG. 8 represents a schematic of a wiring convention used to interconnect components in a system according to the invention.
Figure 8:
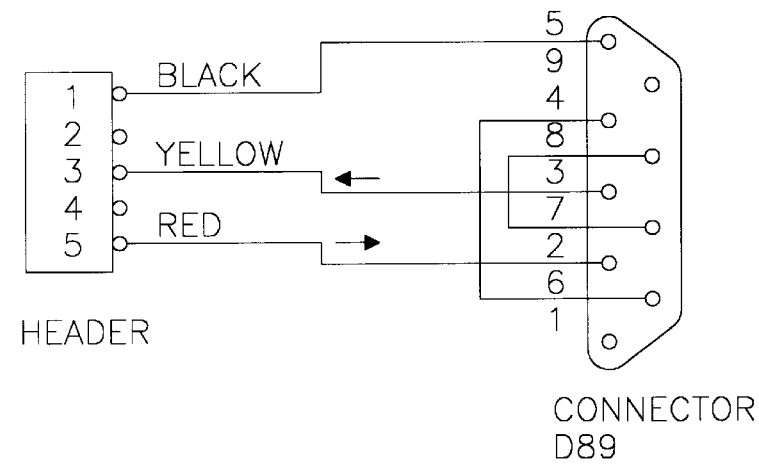
Figure 8:
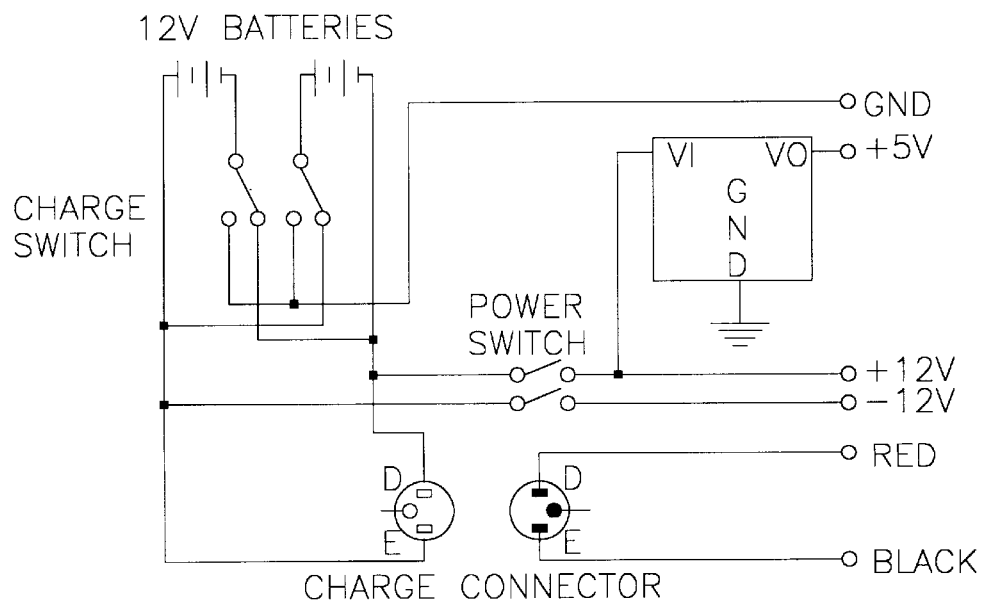

The present invention may also include a display driver 130 for controlling a display that could be included in the indicating means. Alternatively, the display could display operating parameters of the device, such as frequency of the acoustic impulse emitted by the exciting means. The display driver may also be connected to microprocessor 132 through parallel port 129. In one embodiment, the display driver drives a three-digit digital display 110. FIG. 8 shows an embodiment of wiring conventions that may be used for parallel port 129.

Figure 4:
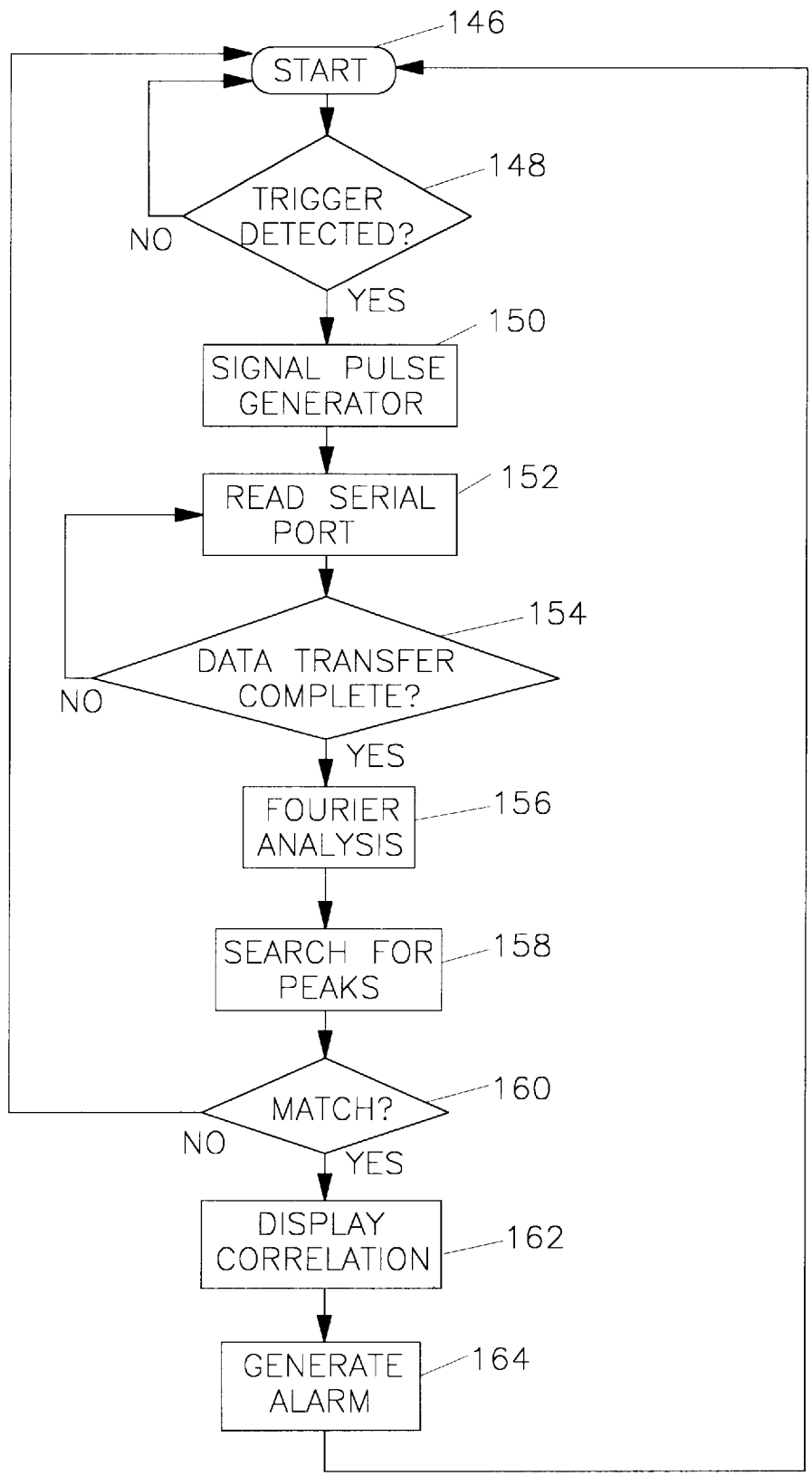
FIG. 4 represents a flow chart showing an embodiment of system operation procedures of a device according to the invention.

FIG. 4 represents an embodiment of a process flow chart showing series of steps according to which the device of the present invention may operate. According to the flow chart shown in FIG. 4, a user of the device initiates an inspection of solid waste in block 146. The user then initiates inspection of the solid waste. To initiate the inspection, the user may direct the exciting means toward the solid waste. Next, an acoustic impulse may be initiated. The acoustic impulse may be generated by activating means for activating the device.

If the embodiment shown in FIG. 1 is being used, the front of satellite housing 102 preferably is directed toward a target item, such as a mass of solid waste, in a trash can, for example, and presses trigger 124. If the microprocessor 132 controls this aspect of the invention, the microprocessor waits until activation of trigger 124 is detected in decision 148 before activating the exciting means. Alternatively, depression of the trigger, or activation of the activating means, could automatically activate the exciting means. If the activating means does not generate a signal to start the device, microprocessor 132 continues to wait until a trigger is detected.

Once the activating means initiates operation of the device, the exciting means produces an acoustic impulse to interrogate the solid waste. In the embodiment shown in FIG. 3, when microprocessor detects trigger 124, the microprocessor initiates generation of exciting means, pulse generator 134 in this embodiment, as indicated by block 150.

In one embodiment, the acoustic impulse is initiated by the leading edge of an approximately 0.5 ms electrical signal generated by the microprocessor. This electrical signal initiates the pulse generator circuit, pulse generator 134 in this embodiment, which drives the exciting means, transmit speaker 118 in this embodiment. Exciting means receives the driving signal and preferably then radiates an acoustic impulse. The acoustic impulse propagates away from the exciting means, housed in satellite housing 102 in the embodiment shown in FIG. 1, and toward the target.

The characteristics of the acoustic impulse produced by the exciting means may vary, depending upon the embodiment and the operating environment, among other factors. We have found with the present invention that an excitation pulse length from about 0.01 ms to about 1 ms would be useful, with a pulse length of about 0.3 ms being preferred. The typical useful frequency range to look for recyclable materials response typically falls between about 10 Hz and about 20 kHz, with a preferred range being from about 30 Hz to about 5 kHz. Any impulsive waveform could be used, with a square doublet pulse waveform being preferred. The amplitude of the acoustic excitation pulse can fall between about 60 dB, referenced at about 10 micropascals, to about 120 dB, with a preferred amplitude being about 95 dB. A single pulse or a pulse train could be used, with a single pulse or a pulse train at approximately 0.5 second intervals being preferred.

After the acoustic pulse has been initiated, the target material will be excited by the acoustic impulse. In response, the target material may start to resonate, as described above. Additionally, the target material may be reflect the acoustic impulse.

Also after microprocessor 132 has initiated an acoustic impulse, the microprocessor waits to receive a return signal, if any, generated by the target at serial port 131. A return signal would be sensed by means to measure the acoustic response. In the embodiment shown in FIG. 3, the measuring means is microphone 120. The measuring means measures any acoustic response produced by the acoustic impulse interacting with the target. The measuring means preferably produces an electronic signal corresponding to any acoustic response it receives.

If the device includes an amplifier circuit, the electronic signal produced by the measuring means may be transmitted to the amplifier circuit. Amplifier circuit 136 may then amplify the electronic signal. The electronic signal may then be digitized. The signal may be digitized by A/D converter 138. After being digitized, the electronic signal may be stored in RAM 140.

Whether or not it is stored in the RAM, after conversion of the electronic signal, the signal may be transported to microprocessor 132. Although any number of known connections may be used, the electronic signal representing the acoustic response of the target may be transmitted to microprocessor by RS-232 driver circuit 142. As the signal is transmitted to the microprocessor, the microprocessor will read the electronic signal from serial port 131, as represented by block 152 in the flow chart shown in FIG. 4.

The microprocessor preferably continues to read information from the serial port until the data transfer is complete, as represented by decision box 154. After the electronic signal is transferred to the microprocessor, the microprocessor preferably starts to analyze it. According to the embodiment shown in FIG. 4, the microprocessor performs a fourier analysis on the electronic signal representing the acoustic response, as represented by block 156 of the flow chart. The fourier analysis 156 may convert the time sampled data into a frequency domain.

The frequency characteristics of the measured acoustic response sensed by the measuring means may be compared to known frequency characteristics of known recyclable materials. These known frequency characteristics may be stored as templates representing known recyclable items. Block 158 of the flow chart shown in FIG. 4 represents the comparison step.

As stated above, the present invention may detect characteristic resonances of certain material(s) to identify the presence of recyclable items among non-recyclable material (s). By measuring the acoustic response generated by a material resulting from an interaction with the acoustic impulse generated by the device, the device can detect the presence of "ringing", or resonating, items measured by measuring means, such as microphone 120. FIG. 2B shows the result of the analysis of three typical measurements made when no resonating structure is present within the measurement range. The operating range of a device according to the present invention may vary from about 1 centimeter to about 2 meters. The effective range may be degraded in noisy environments. FIG. 2E demonstrates the difference that is observed when the same measurement, including the same operating parameters, is taken with a resonating structure, in this case, a glass bottle, within the measurement range of the device. In the trial, the results of which are shown in FIG. 2E, a glass bottle sitting on an open table was interrogated by the acoustic impulse.

According to the present invention, the resonating structure, recyclable material, preferably is excited by the initial acoustic impulse. The resonating structure then reradiates an acoustic response in the form of acoustic energy at characteristic resonance frequencies. In this example, the resonance frequencies measured in the vicinity of about 3,700 Hz and about 4,400 Hz. These resonance characteristics can be exploited to identify the presence of a concealed item made of a recyclable material.

During the comparison, the microprocessor determines whether a sufficient match exists between a known acoustic template and the measured acoustic response signal, represented by decision box 160 of the flow chart. The degree of similarity between the known responses and the response of the target necessary to trigger the indicating means may vary. In some embodiments, the degree of similarity may be displayed to the operator. The operator may then make the decision as to whether items made of recyclable materials are present in the target. According to such an embodiment, microprocessor 132 may transmit the degree of correlation to display driver 130, represented by box 162, to allow the user to read it on a display 110.

The microprocessor 132 may then generate an audible alarm, block 164 of the flow chart, with indicating means, such as alarm 112. Alternatively, the device could include a visual display instead of or in addition to an audible alarm. If no sufficient match is found in the data, as indicated by the alternative branch emanating from decision box 160, microprocessor 132 may restart operation at start box 146.

From the above description it is apparent that the present invention provides a more efficient, safer, more sanitary device that can be used to inspect solid-waste receptacles for the presence of recyclable items.

While the present invention contains many specificities, these should not be construed as limitations on the scope of the invention, but rather as an exemplification of one preferred embodiment thereof. Many other variations are possible. For example a swept frequency or frequency specific acoustic signal could be used to interrogate a target instead of an acoustic impulse.

Additionally, a metal detector could be incorporated into the device to provide the user with another means of detecting some recyclable items which have limited acoustic resonances, such as crushed beverage cans. Furthermore, the device could be modified to provide inspection capabilities for solid-waste collection vehicles, such as garbage trucks. According to such embodiments, a pre-chamber could be developed that would allow a load of trash to be interrogated for recyclables before adding it to the main storage area. Similarly, the device could be modified to allow use in a solid-waste processing and sorting facility. The device could be used to automate the inspection and sorting of the solid-waste stream.

According to one embodiment, the device could include an enclosure that would permit a user to acoustically isolate a target object and increase the signal-to-noise ratio of the measurements. Also, more sophisticated signal processing and analysis could be used to enhance the discrimination capabilities of the device.

Figure 2A:
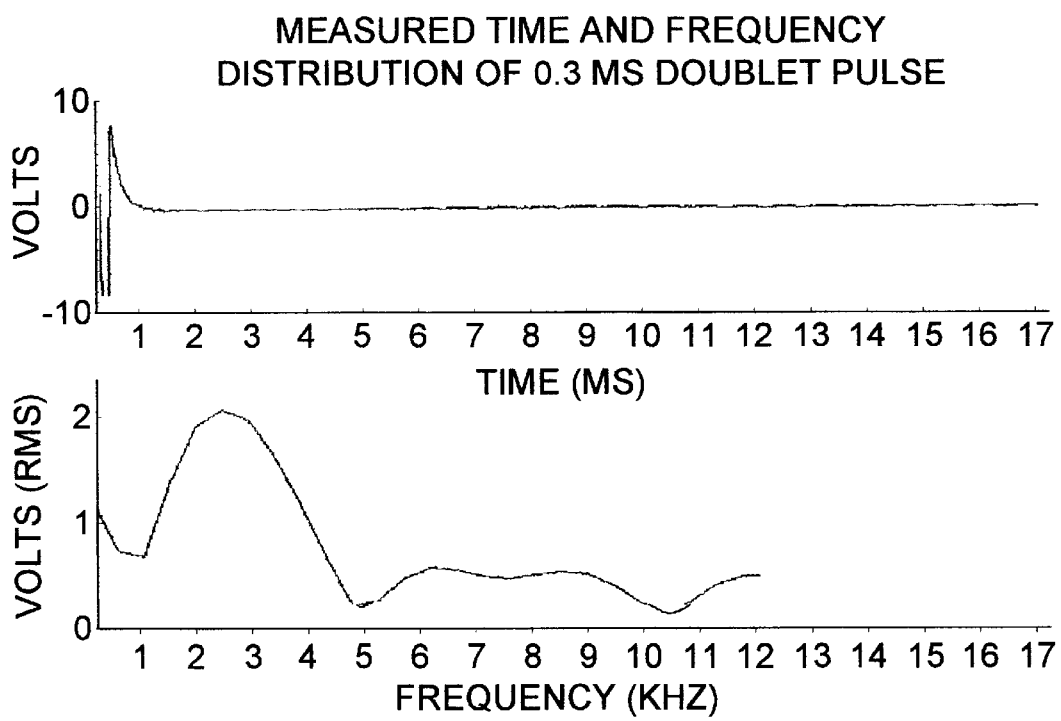
FIG. 2A represents a graph of time and frequency distribution of an acoustic doublet pulse of about 0.3 milliseconds used according to an embodiment of the present invention.
Figure 2B:
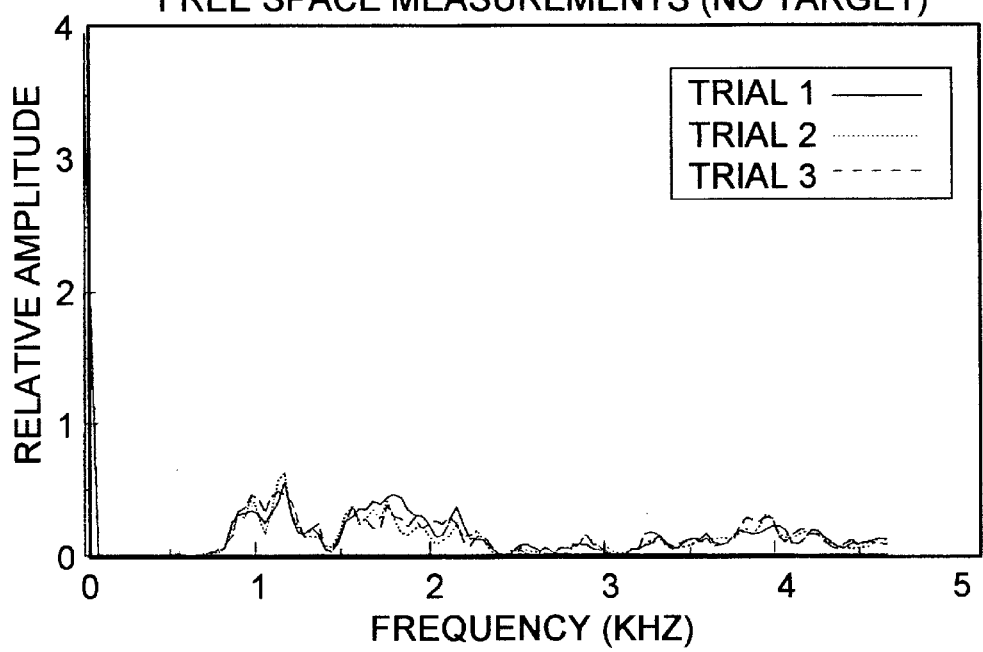
FIG. 2B represents a graph of frequency distribution of a sample measurement of about 25.6 milliseconds for three separate trials wherein the sample measurement is of free space.

The operation of an embodiment of the invention is shown in graph form in FIG. 2A. FIG. 2A shows the time and frequency distribution of a 0.3 millisecond acoustic doublet pulse used for subsequent measurements according to the invention. The upper trace displays the voltage across transmit speaker 118. The lower trace displays the corresponding frequency distribution of the 0.3 millisecond doublet pulse.

The acoustic doublet pulse, generated by sending to transmit speaker 118 a negative, about −8V, electrical pulse followed immediately by a positive, about +8V about 0.3 ms wide electrical pulse. The length of the pulse and the amount of voltage used to generate the pulse may vary. For example, the pulse could be about 0.01 millisecond to about 1 millisecond long. However, for convenience, the acoustic doublet pulse shown in FIG. 2A was employed for all subsequent measurements described herein.

As shown in the lower trace of the graph shown in FIG. 2A, most of the energy from the transmit pulse may be included within a frequency range of about 0 Hz to about 15 kHz. Typically, a useful frequency range for the acoustic pulse generated according to the present invention is between about 30 Hz and about 8 kHz. Although useful, frequencies lower than about 30 Hz may tend to be susceptible to ambient noise pressure levels. On the other hand, while also useful and contemplated by the invention, frequencies higher than about 8 kHz may tend to have higher attenuation ratios, thereby limiting their useful penetration depths through trash bags.

It should be noted that the frequency ranges provided herein are illustrative examples and not exhaustive. Accordingly, the present invention is not limited to these acoustic frequencies.

FIG. 2B is a graph showing three typical measurements made when according to the present invention when no resonating structure is present within the measurement range of the means for acoustic excitation, such as satellite housing 102. In other words, FIG. 2B shows three measurements taken of substantially free, open space. These "free space" measurements demonstrate the frequency distribution of the background noise present in the experimental environment.

To conduct the test, the results of which are shown in FIG. 2B, satellite housing 102 was suspended in air with no target present in the vicinity of transmit speaker 118 or microphone 120. As shown in FIG. 2B, the noise floor of the "free space" measurement has a broad frequency distribution with no distinct resonance frequencies or "peaks".

The measurements shown in FIG. 2B were the result of producing an acoustic doublet pulse of about 0.3 milliseconds. The pulse had a sound pressure level of about 95 dB. FIG. 2B is a graph of the frequency distribution of a 25.6 ms sample measurement. After waiting about 20 milliseconds, a sample of about a 25.6 milliseconds duration was recorded, at a sampling frequency of about 10 kHz. It should be noted that the amplitudes of the sampled acoustic responses shown in FIG. 2B through FIG. 2F are all to a similar relative scale.

Figure 2C:
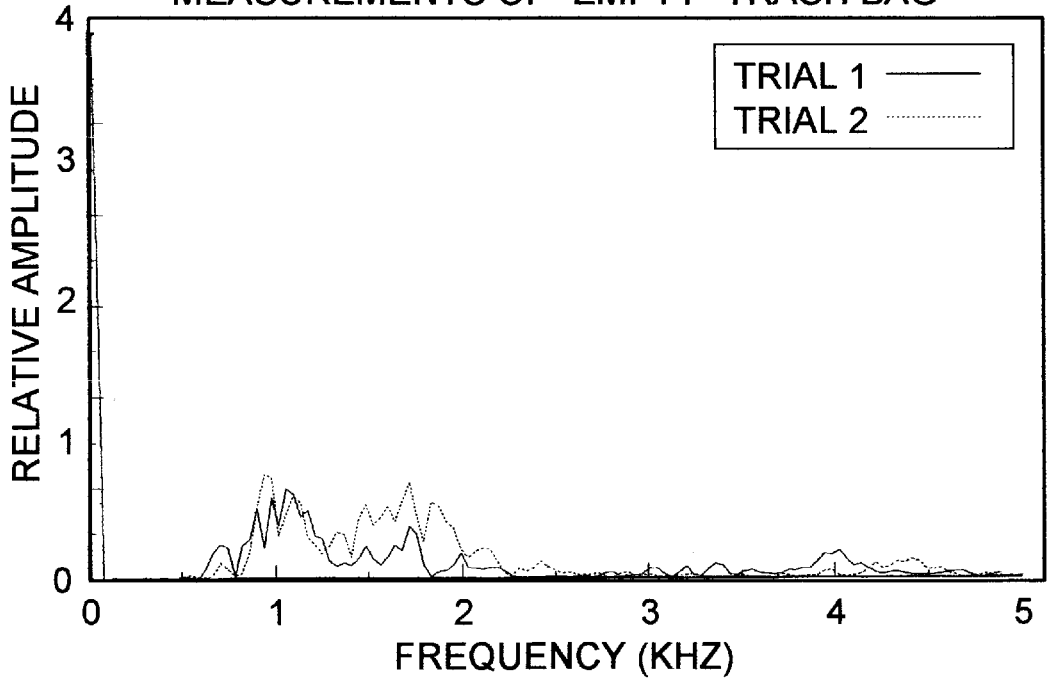
FIG. 2C represents a graph of frequency distribution of a sample measurement of about 25.6 milliseconds for two separate trials of a trash bag that does not contain any resonating recyclable materials.

FIG. 2C represents a graph showing a frequency distribution of a sample measurement of about 25.6 milliseconds. Two trials are shown in FIG. 2C. The trials were conducted on a substantially "empty" trash bag. For purposes of this discussion, a substantially "empty" trash bag is a trash bag that is not filled with any resonating recyclable materials typically detected by the present invention. For these trials, the "empty" trash bag used as a target included crumpled balls of newsprint.

The results shown in FIG. 2C demonstrate differences that are observed between measurements repeated for an "empty" trash bag. The resulting frequency distribution of the recorded acoustic response is substantially similar to the "free space" measurement shown in FIG. 2B. Both FIG. 2B and FIG. 2C show a frequency response that includes a broad distribution with no discernible resonance peaks.

Figure 2D:
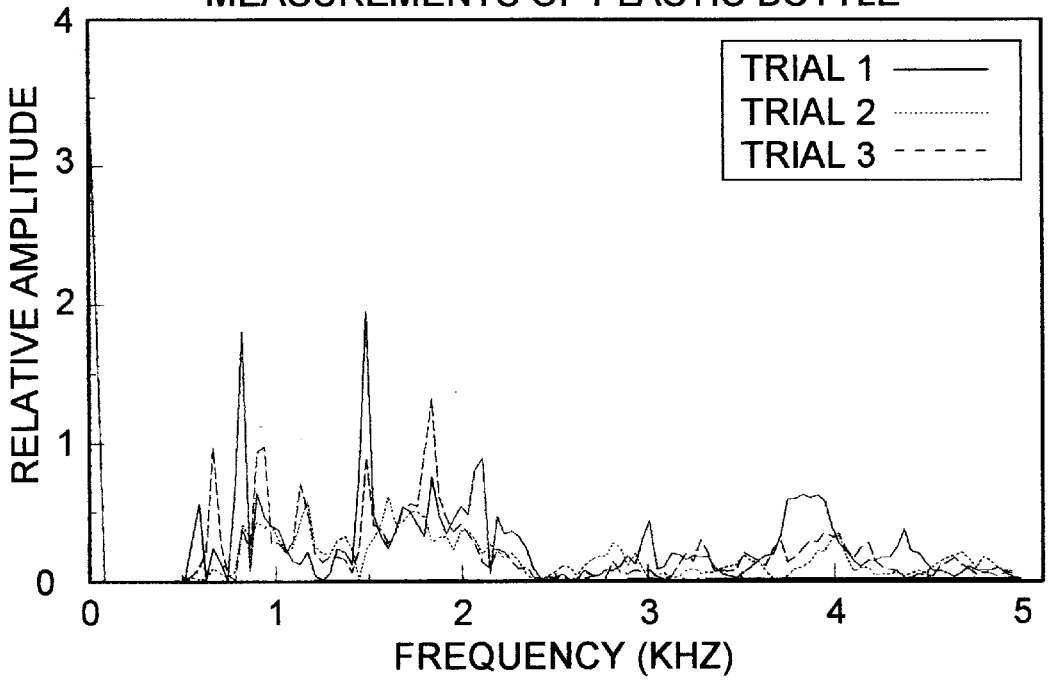
FIG. 2D represents a graph of frequency distribution of a sample measurement of about 25.6 milliseconds for three separate trials of a plastic beverage bottle.
Figure 2E:
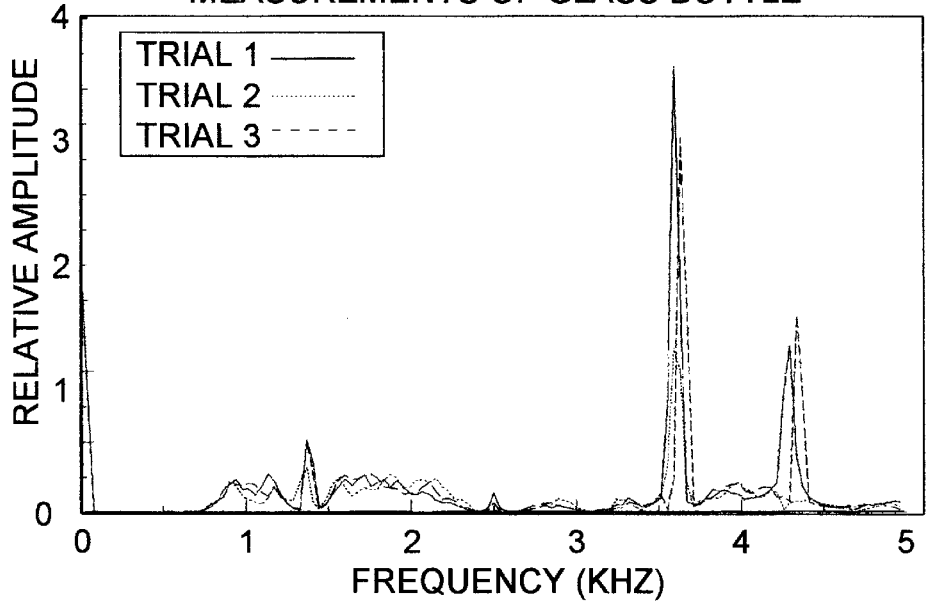
FIG. 2E represents a graph of frequency distribution of a sample measurement of about 25.6 milliseconds for three separate trials of a glass beverage bottle.

FIG. 2D represents a graph showing frequency distribution of a sample measurement of approximately 25.6 milliseconds. Three separate trials are shown in FIG. 2D. The samples were conducted on a substantially empty approximately 64 ounce plastic beverage bottle. The bottle was the type used by Ocean Spray® to hold juice products.

The measurements of the trials, the results of which are shown in FIG. 2D, were made for three different orientations of the bottle. The interrogating acoustic pulse was generated with the bottle approximately 0.3 meters in front of satellite housing 102. In contrast to the graphs shown in FIG. 2B and FIG. 2C, the results shown in FIG. 2D demonstrate sharp frequency peaks measured in the vicinity of about 0.8 kHz and about 1.5 kHz. The frequency peaks result from the resonating structure of the beverage bottle. The bottle acts as a narrow filter and selectively reradiates acoustic energy at the resonance frequency of the bottle when the bottle is excited by the above-described acoustic impulse. These resonance peaks may be used by the present invention to detect the presence of recyclable items within non-resonating solid waste.

FIG. 2E represents a graph showing frequency distribution of a sample measurement of about 25.6 milliseconds. Three separate trials are shown in FIG. 2E. The resonating recyclable material in the test was a substantially empty sixteen ounce glass beverage bottle used by the Veryfine® Co. to hold their juice products.

FIG. 2E shows the resonance peaks resulting when such a bottle is acted upon by the acoustic impulse described below. The measurements were made for three different orientations of the bottle. The bottle was located approximately 0.3 meters in front of satellite housing 102. Although the glass bottle measurements demonstrate different frequency and amplitude characteristics than the plastic bottle, the underlying principle of detection is substantially similar. The large peaks in the graphs shown in FIG. 2E in the vicinity of about 3.6 kHz and about 4.3 kHz can be used to detect the presence of recyclable items within non-resonating solid waste.

Figure 2F:
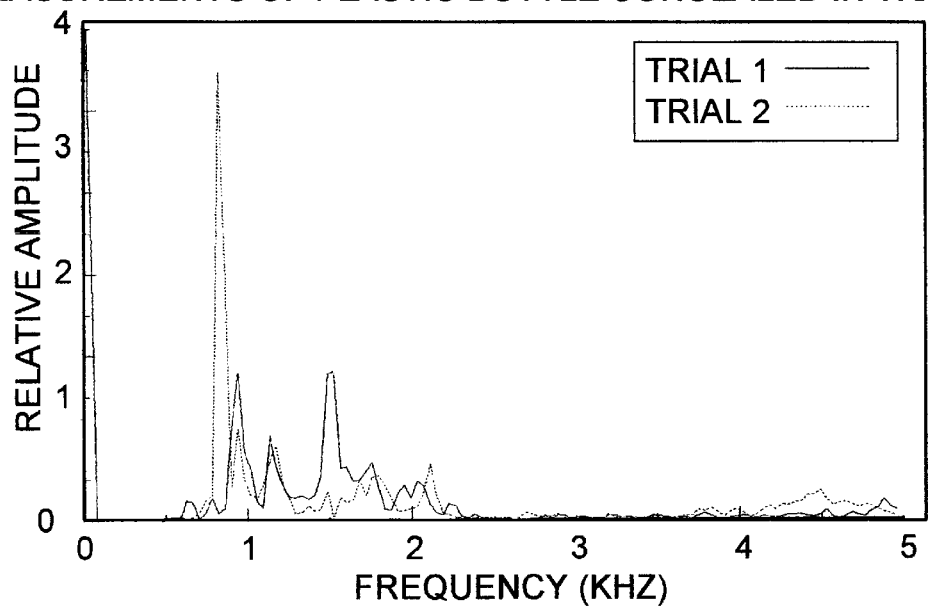
FIG. 2F represents a graph of frequency distribution of a sample measurement of about 25.6 milliseconds for three separate trials of a plastic beverage bottle concealed within a trash bag filled with crumpled balls of newsprint.

FIG. 2F represents a graph showing frequency distribution of a sample measurement of about 25.6 milliseconds. FIG. 2F shows the results for two separate trials. In the trials, a plastic 64 ounce beverage bottle was concealed within a trash bag filled with crumpled balls of newsprint.

The measurements shown in FIG. 2F were made with the surface of the trash bag approximately 0.3 meters away from the front of satellite housing 102. As shown in FIG. 2F, the frequency peaks located near about 0.8 kHz and about 1.5 kHz closely match the location of the previously measured peaks of the plastic bottle shown in FIG. 2D.

By comparing the measured peaks resulting from the interrogation of an unknown sample to known frequency signatures, it is possible to determine the presence of recyclable item(s). It is important to note that the present invention employs information concerning specific resonance peaks for items made of particular recyclable materials to identify the presence of similar items in non-resonating solid waste. It may also be useful to utilize any discernible frequency spike in a predetermined range or ranges as an identifying signature to reveal the presence of recyclable items. We have found that sharp frequency peaks in the range from about 500 Hz to about 4.5 kHz typically result from recyclable items such as glass, plastic, and metal containers. The present invention allows a either a broad search for generalized peaks, or specific identification of selected frequency signatures to identify the presence of recyclable items. One embodiment utilizes simple peak discrimination algorithms with threshold detection to simplify and accelerate the correlation computations. Other, more sophisticated, peak searching techniques may also be employed. As would be well known to those skilled in decision theory, tools such as statistical analysis of multiple measurements could be used to increase the discrimination capability of the present invention.

In this disclosure, there is shown and described only the preferred embodiments of the invention, but, as aforementioned it is to be understood that the invention is capable of use in various other combinations and environments and is capable of changes or modifications within the scope of the inventive concept as expressed herein.

We claim:

1. A device for detecting the presence of items made of recyclable materials randomly located and arranged within randomly arranged solid waste having random characteristics, comprising:

a transmitter for producing acoustic energy of at least one predetermined wavelength in a desired direction, said acoustic energy causing said items made of recyclable materials present within said randomly arranged solid waste to resonate and thereby produce resonated acoustic energy;

a receiver for receiving said resonated acoustic energy, said receiver generating a signal based upon said resonated acoustic energy;

a processor connected at least to said receiver for receiving said signal from said receiver, for analyzing said resonated acoustic energy, for calculating a signature based on said resonated acoustic energy and comparing said calculated signature to known signatures of items made of recyclable materials, thereby detecting composition of the items made of recyclable materials based upon interactions of the materials with the acoustic energy; and means for indicating when said calculated signature substantially corresponds to at least a selected one of said known signatures, thereby indicating the presence of items made of recyclable materials.

2. A device according to claim 1, wherein said known signatures include signatures calculated by analyzing acoustic responses in addition to resonance generated by acoustic energy interacting with known materials.

3. A device according to claim 1, wherein said indicating means includes a display connected to said processor.

4. A device according to claim 1, further comprising:

means for storing said known signatures.

5. A device according to claim 1, wherein:

said acoustic energy produced by said transmitter also reflects off of the solid waste;

said receiver receives said reflected acoustic energy;

said processor analyzes said reflected acoustic energy and calculates said signature based upon said reflected acoustic energy;

said processor compares said signature to known signatures calculated by analyzing acoustic responses generated by acoustic energy reflecting off of said known materials.

6. A device according to claim 1, wherein indicating means includes an alarm for producing an audible signal connected to said processor.

7. A device according to claim 1, further comprising a power source.

8. A device for detecting the presence of items made of recyclable materials randomly located and arranged within a target of randomly arranged material having random characteristics by detecting the composition of the items made of recyclable materials, comprising:

means to excite a target suspected of containing at least one recyclable item with acoustic energy, said acoustic energy causing said randomly located and arranged items made of a recyclable material present within said target of randomly arranged material having random characteristics to resonate and thereby produce resonated acoustic energy;

means to measure said resonated acoustic energy;

means to compare said measured resonated acoustic energy with known resonated acoustic energies corresponding to items made of known recyclable materials, thereby detecting composition of the items made of recyclable materials based upon interactions of the materials with the acoustic energy; and means for indicating a substantial correspondence of said measured resonated acoustic energy from the items made of recyclable materials with at least one of said known resonated acoustic energies, thereby indicating the presence of said items made of recyclable materials.

9. A device according to claim 8, wherein acoustic energy produced by said means to excite a target produces acoustic responses in addition to resonance and comparing means compares said acoustic responses with known acoustic responses of known items made of recyclable materials.

10. A device according to claim 8, wherein said means to excite a target is a transmitter for producing acoustic energy of at least one predetermined wavelength in a desired direction.

11. A device according to claim 8, wherein said means to measure said resonated acoustic energy is a receiver.

12. A device according to claim 8, wherein said means to compare is a processor.

13. A device according to claim 8, wherein said means to indicate is an alarm.

14. A method for detecting items made of recyclable materials randomly arranged and located in randomly arranged solid waste having random characteristics, comprising the steps of:

generating acoustic energy of at least one predetermined wavelength;

directing said acoustic energy in the direction of solid waste, thereby causing items made of recyclable materials within the solid waste to resonate and thereby produce resonated acoustic energy;

receiving said resonated acoustic energy with a receiver;

calculating a signature of said resonated acoustic energy by analyzing said resonated acoustic energy, thereby detecting composition of the items made of recyclable materials based upon interactions of the materials with the acoustic energy; and comparing said calculated signature with known signatures of items made of recyclable materials; and indicating when said calculated signature substantially corresponds to at least one of said known signatures, thereby indicating the presence of items made of recyclable materials.

15. A method according to claim 14, wherein said known signatures include known signatures calculated by analyzing resonated acoustic energy generated by acoustic energy interacting with known items made of known recyclable materials.

16. A method according to claim 14, further comprising the step of:

indicating when said calculated signature substantially corresponds to at least one of said known signatures.

17. A method according to claim 14, wherein generated acoustic energy is ultrasonic.

18. A method according to claim 14, wherein: said generated acoustic energy also reflects off of surface of materials within the solid waste;

said reflected acoustic energy is received;

said signature includes said reflected acoustic energy;

said signature is based on said reflected acoustic energy; and said calculated signature is compared with known signatures calculated by analyzing reflected acoustic energy generated by acoustic energy interacting with know materials.

* * * * *